US005474770A

United States Patent [19]
Broly et al.

[11] Patent Number: 5,474,770
[45] Date of Patent: Dec. 12, 1995

[54] BIOLOGICAL SUPPORT FOR CELL CULTURES CONSTITUTED BY PLASMA PROTEINS COAGULATED BY THROMBIN, ITS USE IN THE PREPARATION OF KERATOCYTE CULTURES, THEIR RECOVERY AND THEIR TRANSPORT FOR THERAPEUTIC PURPOSES

[75] Inventors: Hervé Broly, Houplines; Vincent Ronfard, Lambersart, both of France

[73] Assignee: Centre Regional de Transfusion Sanguine de Lille, Lille, France

[21] Appl. No.: 850,260

[22] Filed: Mar. 12, 1992

Related U.S. Application Data

[63] Continuation of Ser. No. 444,967, Dec. 4, 1989, abandoned.

[30] Foreign Application Priority Data

Dec. 6, 1988 [FR] France .................................. 88 15950

[51] Int. Cl.⁶ ............................ C12N 5/08; C07K 14/745; A01N 1/02; A61F 2/10
[52] U.S. Cl. ................ 424/94.64; 424/530; 435/240.21; 435/240.243; 435/1.1; 435/214; 514/12; 530/381; 530/382; 623/15
[58] Field of Search ......................... 435/240.23, 240.21, 435/240.243, 1, 214; 530/381, 382; 623/15; 424/530, 94.64; 514/12

[56] References Cited

U.S. PATENT DOCUMENTS

| | | | |
|---|---|---|---|
| 2,469,193 | 5/1949 | Cohn ........................................ | 530/831 |
| 2,533,004 | 12/1950 | Ferry et al. ............................. | 530/381 |
| 3,920,625 | 11/1975 | Andersson et al. ...................... | 530/831 |
| 4,414,976 | 11/1983 | Schwarz et al. ......................... | 530/381 |
| 4,427,650 | 1/1984 | Stroetmann ............................. | 530/381 |
| 4,442,655 | 4/1984 | Stroetmann ............................. | 530/381 |
| 4,452,893 | 6/1984 | Ng et al. ................................. | 435/240.3 |
| 4,485,096 | 11/1984 | Bell ........................................... | 623/1 |
| 5,260,420 | 11/1993 | Burnout-Radosevich et al. ...... | 530/382 |

FOREIGN PATENT DOCUMENTS

| | | |
|---|---|---|
| 0085923 | 1/1983 | European Pat. Off. . |
| 0143648 | 11/1984 | European Pat. Off. . |
| 0305243 | 7/1988 | European Pat. Off. . |

OTHER PUBLICATIONS

Nuzzolo, et al. Tissue Culture Techniques pp. 84–85 Warren H. Green, Inc. St. Louis, Mo. 1983.
Hunyadi, et al. Keratinocyte Transplantation: Covering of Skin Defects by Autologous Keratinocytes.
Biological Abstracts vol. 85 No. 5 Abstract 43762 Mar., 1988.
Cohn et al. Preparation and Properties of Serum and Plasma Proteins IV. J. American Chemical Society vol. 68 pp. 459–475 Mar., 1946.
Search Report from FR 88 15950.
Ronfard et al., "Use of human keratinocytes . . . treatment of burn wounds," *Burns*, (1991) vol. 17, No. 3, pp. 181–184.

*Primary Examiner*—Margaret Moskowitz Parr
*Assistant Examiner*—Ron Schwadron
*Attorney, Agent, or Firm*—Birch, Stewart, Kolasch & Birch

[57] ABSTRACT

The present invention relates to a biological support for cell cultures formed by the coagulated mixture of a concentrate of plasma proteins and thrombin.

The protein concentrate is obtained by precipitating fresh plasma with ethanol and contains balanced proportions of fibrinogen, Factor XIII and fibronectin. The thrombin concentration is adjusted to obtain the desired consistency of the support coagulated in the form of a film.

The biological support is preferably used for preparing a culture of keratinocytes, recovering them in the form of a reconstituted tissue and transporting same. The reconstituted tissue is thus particularly suitable for use as a graft.

16 Claims, No Drawings

BIOLOGICAL SUPPORT FOR CELL CULTURES CONSTITUTED BY PLASMA PROTEINS COAGULATED BY THROMBIN, ITS USE IN THE PREPARATION OF KERATOCYTE CULTURES, THEIR RECOVERY AND THEIR TRANSPORT FOR THERAPEUTIC PURPOSES

This application is a continuation of application Ser. No. 07/444,967 filed on Dec. 4, 1989, now abandoned.

BACKGROUND OF THE INVENTION

1. Field of the Invention

The present invention relates to a biological support for cell cultures, constituted by a coagulated mixture of a concentrate of plasma proteins and thrombin, its use in the preparation of keratinocyte cultures and their transport in the form of reconstituted epidermises, and their use for therapeutic purposes.

2. Description of Related Art

The reconstitution in a laboratory of a living skin similar to the human skin from a few cells obtained from a biopsy, or of a simplified skin performing the physiological functions of a normal skin, is being studied extensively In the aim of replacing skin damaged by a serious disease (genetic, etc.) or destroyed by major burns.

The skin is a complex organ composed of three juxtaposed tissues: the epidermis, 85% of which is constituted by keratinocytes which form the impermeable horny layer that isolates the body from the outside environment; the dermis, which comprises cells, including fibrocytes, separated by a connective tissue composed mainly of collagen; the dermis lies on the hypoderma, which includes the cells dedicated to storing fats. Artificial reconstitution of such a complex organ thus poses numerous problems.

The first tissue to have been partially reconstituted in vitro was the dermis, this being achieved by the Bell team (Bell et al.) *Proc. Natl. Aced. Sci.* 76-1979-1274).

Starting with skin biopsies, fibroblasts have been successfully established in cultures, first in monolayers, then, after a number of passages, by dispersing these cells in culture medium containing collagen (extracted from rat's tail tendons), the latter forming a gel and permitting three-dimensional cultures. In such cultures, the fibroblasts can be seen interacting with the matrix of the collagen, organizing it and contracting It as in a normal dermis. This tissue, reconstituted in vitro, is known as an "equivalent dermis". After a few weeks' growth, the mechanical qualities of the equivalent dermis allow it to be used for grafting onto a patient or injured person. It does not appear to be rejected by its host. However, this equivalent dermis is merely a temporary dressing: it cannot restore the the cutaneous barrier function.

Furthermore, the Green team (H. Green et al. Proc. Natl. Aced. Sci. 76, 1979, 5665) has developed a method and a culture medium enabling keratinocytes to be grown for long periods. This method includes inoculating the keratinocytes dispersed with trypsin on a pre-established monolayer of fibroblasts, in particular 3T3 cells, lethally irradiated and which serve as a nutritive layer and as a matrix. The epidermal layer develops very rapidly to form a tissue having a thickness of 3 to 5 cells; it can be grafted onto a patient and continue to differentiate in situ. It has already proved possible to save those suffering from severe burns using this technique (G. Gallico et al. New England J. Med. 311, 1984, 448).

With Green's technique, it is possible to obtain, from a biopsy of two square centimeters an epidermis of one square meter in the space of three weeks.

Recovery of the reconstituted tissue in order to make a graft therefrom still poses a number of technical problems. It is, indeed, necessary to detach the cells from the culture dish, using an enzyme treatment, without dissociating them from one another; during this operation, one always observes a retraction of the cell layer, hence a loss of a certain percentage of the surface area of the graft. Once the reconstituted tissue has been detached, it has to be fastened to a support that enables it to be transported and grafted onto the patient. A vaseline treated gauze dressing is generally used. All these manipulations are delicate and time consuming.

It would thus be highly beneficial to have at one's disposal novel biological supports that can be resorbed in time by the patient who has received the graft and which simplify the handling of the cells. In addition, to ensure their availability, these supports or their constituents would have to lend themselves to preparation and packaging in accordance with industrial processes.

SUMMARY OF THE INVENTION

The Applicant has thus developed a biological support for cell cultures constituted by a mixture of a concentrate of plasma proteins that can be coagulated by thrombin and of the quantity of calcic thrombin that is necessary to activate coagulation.

The coagulation of the plasma proteins in the presence of thrombin is chiefly due to the formation of a polymerized fibrin network which imitates the formation of a blood clot. To form a support suitable for the preparation of cell cultures, coagulation is carried out under conditions conducive to the formation of a film and, more particularly, in Petri flasks or in any flask suitable for cell cultures.

DETAILED DESCRIPTION OF THE INVENTION

The concentrate of plasma proteins has already been described by the Applicant in European patent application 88 401 961 3: it is obtained by precipitating fresh plasma, in two successive treatments using a 10% ethanol solution at 4° C. The concentrate contains over 90% of fibrinogen and, per gram of proteins, at least 0.1 IU of Factor XIII and from 0.03 to 0.1 grams of fibronectin. The concentrate is packaged and freeze dried to preserve It until it is used.

The present invention thus also concerns the concentrate of proteins that can be coagulated by thrombin, specially packaged for preparation of the biological support for cell cultures.

At its time of use, the concentrate is redissolved in a saline aqueous solution or in a solution containing a polyvalent protease inhibitor, preferably aprotinin, at a concentration of 3000 KIU/ml.

To activate the coagulation process, hence the formation of the film serving as a support for the cells, thrombin is added, with or without calcium. The process includes the transformation of fibrinogen into fibrin through the action of thrombin and the polymerization of monomeric fibrin with fibronectin through the action of Factor XIII activated by $Ca^{++}$ ions.

To form the support according to the invention, which is particularly appropriate for cell cultures, the thrombin concentration is preferably adjusted to approximately 10 IU/ml (a far lower concentration than the one used when the desired consistency is different, as in the case of biological glues— patent No. 88 401 961 3, mentioned above).

According to different forms of embodiment of the invention, it is possible to incorporate In the support various additives particularly designed to promote cell multiplication in vitro or in situ and thus favoring the healing of the wound after grafting.

The support can thus contain an additive promoting cell multiplication such as a growth factor and, more particularly, EGF ("epidermal growth factor").

A healing agent or an antibiotic can also be incorporated.

The support according to the invention is particularly advantageous when preparing human keratinocyte cultures. These cells can be either primary cultures derived from skin biopsies obtained from a patient and that have undergone between 1 and 4 passages in 1/15 to 1/20 dilutions, or cells preserved in the form of banks in liquid nitrogen.

These keratinocytes established in a confluent layer are trypsinized and replaced in suspension in an appropriate culture medium at the time of their seeding on the support according to the invention.

The use of the biological support according to the invention can be adapted in three different ways.

According to a first method of use, the biological support is prepared in the form of a film, by mixing its two constituents in a culture dish; a suspension of keratinocytes is seeded on this film, in an appropriate culture medium. When the keratinocyte culture has become confluent or semi-confluent, it forms a replacement tissue that can be recovered directly as a graft that can be detached using forceps and transported from the dish to the patient, on whom it is applied as it is, without there being any need for a temporary support such as gauze. This makes for a considerable saving in working time and 100% recovery of the tissue grown.

According to another method of using the support according to the invention, the two constituents of the support are mixed with the keratinocytes suspension in such a way as to integrate the cells in the film that will be formed subsequently. According to this method, the two constituents can be mixed with the cell suspension in a culture dish and then used as a graft, as in the method described above; It can also be carried out directly on the patient's wound, prepared to receive a graft, in particular by spraying the biological support and the cells using a vector gas (nitrogen) at a pressure of 2 to 2.5 bars.

According to another method of using the support according to the invention, its two constituents are mixed on a cell layer of keratinocytes pre-established In a culture dish, in such a way that the cells are coated with the film that has formed and can thus be detached and transported in order to be applied as a graft.

The following examples serve to illustrate the invention without thereby restricting its scope.

Example I—Preparation of the biological support for cell cultures

A biological support for cell cultures is prepared by mixing a concentrate of coagulable plasma proteins and the quantity of calcic thrombin necessary to activate coagulation.

A. Preparation of the concentrate of plasma proteins

The preparation of the protein concentrate has already been described by the Applicant in European patent application No. 88 401 961 3. To summarize, use is made of non cryoprecipitated human plasma; it is precipitated twice in succession in a 10% solution of ethanol at a pH of 7.2 and a temperature of 4° C. Between two successive precipitations, the product undergoes a virus inactivation treatment. The precipitate, separated from the supernatant by centrifuging, is washed in ethanol at 4° C. and re-centrifuged. The precipitate is replaced in suspension in a Tris/citrate buffer, adjusted to a protein concentration of approximately 35 g/l and lysine is added thereto at a final concentration of 0.1 to 0.2 g per gram of proteins. After diafiltration to remove the alcohol and the citrate, and to adjust the ionic force, the concentrate is packaged in flasks and freeze dried.

This protein concentrate contains, per gram of proteins, at least 0.9 g of fibrinogen, 0.03 to 0.06 g of fibronectin and 0.15 to 0.30 IU of Factor XIII.

B. Preparation of the support for cell cultures

The protein concentrate described above is replaced in suspension in an aqueous solution, with or without aprotinin, at a concentration of 3000 KIU/ml (kallikrein inhibitor units/ml).

This solution is mixed with an equal volume of calcic thrombin at 10 IU/ml.

For a Petri dish, with a diameter of 10 cm, use is made of 2 ml of protein suspension and 2 ml of thrombin, these two solutions being injected simultaneously using two syringes interconnected by a mixing coupling. The Petri dish is shaken to obtain uniform distribution and the preparation is then allowed to rest for 15 to 20 minutes. It forms a film that covers the dish.

The culture dishes are of the type "non treated for cell cultures", which ensures that the support does not adhere permanently, thus facilitating its subsequent recovery.

This film is then covered with cell culture medium. This medium is renewed several times until the osmotic pressure of the film is stabilized within a range compatible with the physiology of the cells, i.e. between 260 and 340 mosM (milliosmoles).

Alternatively, the reconstituted protein concentrate can be dialyzed before it is mixed with the thrombin.

Example 2—Preparing a keratinocytes culture on the biological support

Use is made of primary cultures of keratinocytes prepared using Green's classical technique from skin biopsies obtained from a patient's skin (or an embryo's skin to form foetal cell banks). These primary cultures can undergo 4 to 5 passages in 1/10 dilution.

A layer of confluent keratinocytes is trypsinized, replaced in suspension in culture medium and seeded in 1/10 dilution on a Petri dish covered with a film of the biological support described in example 1.

After a few hours, the cells adhere to the support, where they then multiply normally until they form a fragment of confluent epidermis having a thickness of 3 or 4 cell layers.

This fragment of reconstituted epidermis, adhering to the support, can be detached from the culture dish using forceps and applied as it is to a wound prepared to receive a graft.

As the cells adhere to the support, there is no need to attach the reconstituted epidermis to another support such as the vaseline treated gauze which has to be used with the other types of culture. This makes for a considerable saving in working time, it being possible to handle 40 Petri dishes an hour as opposed to the 4 Petri dishes of the conventional techniques.

Furthermore, this support stands up well to handling and does not retract at the time of detachment, which makes it possible to recover 100% of the surface area of the cell layer of the culture.

Example 3—Recovery of a pre-established cell layer using the biological support Keratinocytes are inoculated according to Green's conventional method, in a Petri dish covered with a layer of lethally irradiated fibroblasts.

When the sheet of keratinocytes is confluent and formed of several layers of cells, the culture medium is removed, an EDTA solution is added for 1 hour 30 minutes, this being followed by washing twice with PBS. The biological support is then poured directly onto the layer of cells, in accordance with the method described in example 2.

When the film is formed over the cells, it can be detached using forceps and used as a graft, as in the preceding example.

Example 4—Incorporation of the cells into the biological support

A syringe of protein solution and a syringe of thrombin containing the keratinocytes in suspension are prepared. These keratinocytes can be taken from a fresh, trypsinized culture or from a bank of cells preserved in liquid nitrogen.

The two syringes are interconnected by means of a mixing coupling and the support containing the cells is sprayed onto the Petri dish (or onto the wound to receive the graft); the cells are thus held in the film during its coagulation. The spraying can be carried out using a vector gas (nitrogen at a pressure of 2 to 2.5 bars).

This spraying does not denature the cells and the cell layer can be observed to reform, in culture in vitro. The cells should thus multiply normally or practically normally, when the mixture is sprayed, in a very thin layer, directly onto a wound.

We claim:

1. A biological support for skin grafts, which comprises approximately 10 IU/ml of calcic thrombin and a mixture of a concentrate of proteins that can be coagulated by thrombin, obtained by treating noncryoprecipitated plasma with ethanol and containing proportions of coagulable fibrinogen, Factor XIII, and plasma fibronectin sufficient to form a biological support in the presence of calcic thrombin.

2. The biological support according to claim 1, wherein the concentrate of coagulable plasma proteins contains over 90% of fibrinogen and, per gram of proteins, and at least 0.1 IU of Factor XIII and 0.03 to 0.1 grams of fibronectin per gram of protein.

3. The biological support according to claim 2, wherein the protein concentrate is obtained by precipitating fresh plasma, in two successive treatments with a 10% solution of ethanol at 4° C.

4. The biological support according to claim 1, wherein the protein concentrate is freeze dried.

5. The biological support according to any one of claims 1 to 3, wherein the protein concentrate is placed in suspension in an aprotinin solution, said aprotinin solution having a concentration of 3000 KIU/ml.

6. The biological support according to any one of claims 1 to 3, wherein it contains, as an additive, an enhancer of cell multiplication.

7. The biological support according to any one of claims 1 to 3, wherein it contains, as an additive, an antibiotic.

8. A method of using the biological support according to any one of claims 1 to 3, which comprises preparing a culture of human keratinocytes, fetal or adult, on said biological support to form a skin replacement tissue and recovering, transporting and applying said skin replacement tissue as a graft.

9. The method according to claim 8, wherein said protein concentrate and calcic thrombin are mixed in such a way as to form a uniform film in a culture dish and the keratinocytes in suspension in culture medium are seeded on said film.

10. The method according to claim 8, wherein said protein concentrate and calcic thrombin are mixed with a suspension of keratinocytes in such a way as to integrate the cells into the film subsequently formed.

11. The method according to claim 9, wherein the keratinocytes suspension is obtained after dispersion of a fresh, pre-established cell layer.

12. The method according to claim 9, wherein the keratinocytes suspension is obtained from a bank of cells preserved in liquid nitrogen.

13. A method of using a biological support according to any one of claims 1 to 3, which comprises recovering a culture of human keratinocytes, fetal or adult, pre-established on the biological support of any one of claims 1 to 3, and transporting said culture and biological support to a patient in need thereof.

14. The method according to claim 13, wherein said protein concentrate and calcic thrombin are mixed on the pro-established cell layer in a culture dish.

15. The biological support according to claim 1, wherein said concentrate contains more than 90% fibrinogen per gram of protein.

16. A composition which comprises a culture of human keratinocytes attached to said biological support of any one of claims 1 to 3.

\* \* \* \* \*